(12) United States Patent
Blatter et al.

(10) Patent No.: US 9,169,262 B2
(45) Date of Patent: Oct. 27, 2015

(54) CRYSTALLINE SALTS OF ASENAPINE WITH ORGANIC DI-ACIDS AND TRI-ACIDS

(75) Inventors: Fritz Blatter, Reinach (CH); Katharina Reichenbächer, Rheinfelden (DE)

(73) Assignee: SANDOZ AG, Basel (CH)

( * ) Notice: Subject to any disclaimer, the term of this patent is extended or adjusted under 35 U.S.C. 154(b) by 0 days.

(21) Appl. No.: 14/116,110

(22) PCT Filed: May 15, 2012

(86) PCT No.: PCT/EP2012/058963
§ 371 (c)(1),
(2), (4) Date: Jan. 16, 2014

(87) PCT Pub. No.: WO2012/156383
PCT Pub. Date: Nov. 22, 2012

(65) Prior Publication Data
US 2014/0128444 A1    May 8, 2014

(30) Foreign Application Priority Data

May 17, 2011    (EP) ..................................... 11166311

(51) Int. Cl.
| | | |
|---|---|---|
| *C07D 491/044* | (2006.01) | |
| *C07D 491/04* | (2006.01) | |
| *C07C 55/08* | (2006.01) | |
| *C07C 59/42* | (2006.01) | |

(52) U.S. Cl.
CPC ............ *C07D 491/044* (2013.01); *C07C 55/08* (2013.01); *C07C 59/42* (2013.01); *C07D 491/04* (2013.01)

(58) Field of Classification Search
CPC ................................................... C07D 491/044
USPC .......................................... 514/410; 548/421
See application file for complete search history.

(56) References Cited

FOREIGN PATENT DOCUMENTS

| | | |
|---|---|---|
| EP | 0 569 096 A1 | 11/1993 |
| GB | 1 567 862 A | 5/1980 |
| WO | WO 2006/106135 A1 | 10/2006 |
| WO | WO 2008/003460 A1 | 1/2008 |

OTHER PUBLICATIONS

C.W. Funke et al., "Physico-Chemical Properties and Stability of Trans-5-Chloro-2-Methyl-2,3:6,70 Oxepino-4,5-C) Pyrrolidine Maleate", Arzneimittel Forschung. Drug Research, ECV Editio Cantor Verlag, May 1, 1990, vol. 40, No. 5, pp. 536-539.
International Search Report, International Application No. PCT/EP2012/058963 mailing date Jun. 28, 2012.

*Primary Examiner* — Shawquia Jackson
(74) *Attorney, Agent, or Firm* — Arent Fox LLP

(57) ABSTRACT

Novel crystalline salts of Asenapine (I) with organic di-acids and tri-acids and to methods of their preparation are disclosed along with related pharmaceutical compositions and methods of treating psychotic diseases or disorders.

12 Claims, 1 Drawing Sheet

CRYSTALLINE SALTS OF ASENAPINE WITH ORGANIC DI-ACIDS AND TRI-ACIDS

CROSS-REFERENCE TO RELATED APPLICATION

Figure 1:
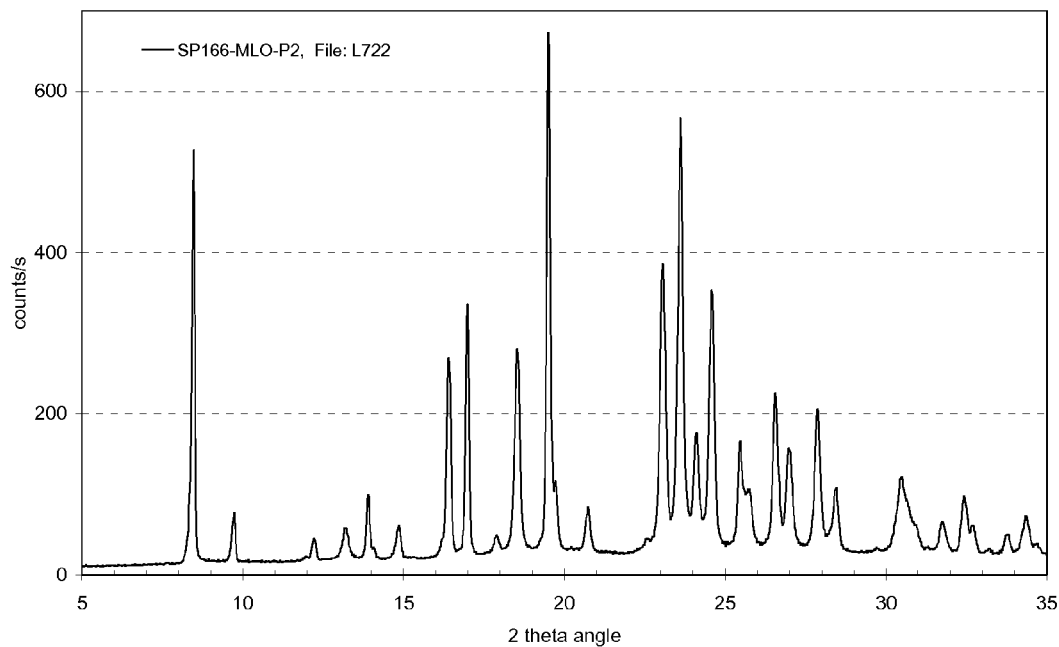

This application is a National Stage entry of International Application No. PCT/EP2012/058963, filed May 15, 2012, which claims priority to European Application No. 11166311.8, filed May 17, 2011, the entire specifications, claims and drawings of which are incorporated herewith by reference.

FIELD OF THE INVENTION

The invention relates to novel crystalline salts of Asenapine with organic di-acids and tri-acids and to methods of their preparation. Furthermore the invention relates to the use of the novel salts in pharmaceutical compositions and to the use of the novel salts as medicaments, preferably in the treatment of psychotic diseases or disorders such as schizophrenia and acute mania associated with bipolar disorder.

BACKGROUND PRIOR ART

Asenapine, trademark Saphris®, chemically trans-5-chloro-2-methyl-2,3,3a,12b-tetrahydro-1H-dibenz[2,3:6,7]oxepino[4,5-c]pyrrole, in sublingual dissolving tablet form, has been approved in the US in August 2009 for the acute treatment of adult patients with schizophrenia and as monotherapy for acute mania or mixed episodes associated with bipolar disorders. The FDA has recently approved its use as ongoing maintenance treatment for schizophrenia and as adjunctive therapy with lithium or with valproate for bipolar 1 disorder.

Certain crystalline addition salts of Asenapine, for instance a fumarate (EP 0569096), salts with sulfonic acids (WO98/54186), and a pamoate or hemipamoate salt (EP569096), are described in the literature. The pamoate salt is disclosed to be amorphous and the hemipamoate salt is a mixture of amorphous and crystalline phase, wherein the palmitate is described as oil. The marketed form is the maleate salt, which is disclosed to exist in polymorphic forms (WO 2006/106135). The known Asenapine salts have a low solubility in water. For example, Funke et. al. (Arzneim.-Forsch./Drug Res. 40, 1999, 536-539) reports that a saturated solution of the maleate salt of Asenapine at 23° C. has a concentration of 5.8 mg/ml at pH=4.4 (see also US2008/0306133 A1 regarding the solubility of Asenapine. This translates into a free base solubility of about 4.1 mg/ml. WO2009/135091 also discloses Asenapine and related compounds and salts thereof for treating a neuronal or non-neuronal indication. Peter van Hoof et al. (Amorphous Pharmaceutical Materials, September 2009, Amsterdam) describe a method for validation of a drug product of Asenapine in solid state form.

The discovery of new salts of a pharmaceutically useful compound provides a new opportunity to improve the performance characteristics of a pharmaceutical product. It enlarges the repertoire of materials that a formulation scientist has available for designing, for example a pharmaceutical dosage form of a drug with targeted release profile or other desired characteristic.

A further aspect of the invention is to provide new forms of Asenapine with a smaller tendency towards formation of polymorphic forms. Polymorphism is well known in the pharmaceutical industry and active pharmaceutical ingredients (API) that exist in multiple crystalline forms (polymorphs) are generally undesired, because different polymorphs exhibit different physico-chemical properties, and in particular, if a solubility difference between two polymorphs is found this may have a direct impact on the bioavailability. As a consequence, if an API exists in multiple crystalline forms, greater efforts are often necessary to control the manufacturing process, to develop analytical methods, to set-up additional specifications and controls to guarantee the safety and consistency during the shelf-life of the drug product. This increases the costs for the end product. It is therefore highly desirable to provide Asenapine in a form that shows a good solubility and bioavailability profile as well as stability, e.g. against a potential phase conversion.

Furthermore, a premise for a sublingual dissolving tablet form is an active ingredient exhibiting good solubility in a fast dissolving matrix. It is an objective of the invention to provide pharmaceutically acceptable forms of Asenapine that may have a good solubility. It is also an object of the invention to provide Asenapine in a form that may have a good chemical and/or physical stability and/or good processability, both during its preparation and in the preparation of pharmaceutical compositions containing Asenapine.

SUMMARY OF THE INVENTION

Surprisingly, it was found that the crystalline salts of Asenapine with organic di-acids or tri-acids according to the invention may have beneficial properties regarding solubility and stability. In particular, the novel addition salts of Asenapine with organic acids may not show polymorphism and may meet above defined criteria for solubility, chemical stability and processability and may thus avoid the known polymorph issues with the marketed maleate.

The invention thus refers to the following numbered embodiments:

(1) A crystalline polymorphically stable salt, preferably in anhydrous form, of trans-5-chloro-2-methyl-2,3,3a,12b-tetrahydro-1H-dibenz[2,3:6,7]oxepino[4,5-c]pyrrole (Asenapine) with an organic di-acid or tri-acid, wherein said salt has a solubility in water at 25° C. of at least 2.0 mg/ml, preferably at least or more than 2.4 mg/ml, calculated as free base and wherein the polymorphic stability is such that essentially all, preferably at least 90 wt. %, of said salt does not change its crystal structure upon stirring in acetonitrile for 96 hours at a temperature of 20° C.

(2) The crystalline salt of item 1, wherein the molar ratio of Asenapine to the organic di-acid or tri-acid in said salt is between 1:1.3 to 1.3:1.

(3) The crystalline salt of item 1 or 2, wherein the organic di-acid or tri-acid is a carboxylic di-acid or carboxylic tri-acid, preferably a saturated $C_3$-$C_{14}$ carboxylic di-acid or tri-acid.

(4) The crystalline salt of any of items 1-3, wherein the organic di-acid or tri-acid is malonic acid or citric acid, preferably said salt is an anhydrous salt of Asenapine with malonic acid or citric acid.

(5) A crystalline salt of asenapine being preferably of any of items 1-4, which comprises or consists of (i) crystalline Asenapine malonate form I or (ii) crystalline Asenapine citrate form I, wherein (i) crystalline Asenapine malonate form I is characterized by X-ray powder diffraction reflections (Cu Kα radiation) comprising peaks at two theta angles of about 19.5°±0.2°, 23.7°±0.2°, 8.5°±0.2°, 23.1°±0.2°, and 24.2°±0.2°, and/or (ii) crystalline Asenapine citrate form I is characterized by X-ray powder diffraction reflections (Cu Kα radiation)

comprising peaks at two theta angles of about 15.5°±0.2°, 15.3°±0.2°, 12.6°±0.2°, 23.2°±0.2°, and 19.4°±0.2°.

(6) A process for preparing a crystalline polymorphically stable salt according to any of items 1-5, preferably in anhydrous form, of trans-5-chloro-2-methyl-2,3,3a,12b-tetrahydro-1H-dibenz[2,3:6,7]oxepino[4,5-c]pyrrole (Asenapine) with an organic di-acid or tri-acid comprising the steps of:
  a) combining Asenapine free base with an organic di-acid or tri-acid in an organic solvent or organic solvent mixture, optionally comprising water, and
  b) obtaining said crystalline polymorphically stable Asenapine salt.

(7) The process of item 6, wherein the organic di-acid or tri-acid is a carboxylic di-acid or carboxylic tri-acid, preferably a saturated $C_3$-$C_{14}$ carboxylic di-acid or tri-acid, further preferred malonic acid or citric acid.

In step (a), the organic di-acid or tri-acid can be added in pure form or as a solution in the solvent or solvent mixture used in step (a).

(8) The process of item 6 or 7, wherein step (a) is carried out in the presence of seed crystals.

In step (a), malonic acid can e.g. be added in pure form or as a solution in the solvent or solvent mixture used in step (a). In step (a), malonic acid can e.g. be added in pure form or as a solution in the solvent or solvent mixture used in step (a).

(9) The process of any of items 6-8, wherein the crystalline polymorphically stable Asenapine salt obtained in step (b) is crystalline Asenapine malonate form I or crystalline Asenapine citrate form I.

(10) The process of any of items 6-9, wherein the solvent or solvent mixture comprises or consists of one or more organic solvents from the group consisting of esters, preferably acetic acid $C_1$-$C_6$ alkylesters, most preferably ethylacetate; alcohols, preferable $C_1$-$C_5$ alcohols, e.g. methanol, ethanol or propanol or mixtures thereof; mixtures of acetic acid $C_1$-$C_6$ alkylesters and $C_1$-$C_6$ alcohols, preferable ethyl acetate and a $C_1$-$C_5$ alcohol, preferably ethanol; ketones, preferably acetone; combinations of acetic acid $C_1$-$C_6$ alkylesters; optionally in the presence of water.

(11) The process of any of items 6-10, wherein step (a) is carried out at a temperature of between 15° C. and the boiling temperature of the solvent or solvent mixture preferably under stirring. A temperature of between 15° C. and 25° C. is preferred in step (a). After stirring the reaction mixture for a time period of between 1 hour and two weeks, preferably between one day and one week, the reaction mixture can be cooled to a temperature of between 0° C. and 15° C. or the organic solvent/solvent mixture can be partly removed for completion of crystallization.

(12) Crystalline polymorphically stable salt, in particular in anhydrous form, of Asenapine with an organic di-acid or tri-acid according to any of items 1-5 or obtained or obtainable according to any of items 6-11 as medicament, preferably for the treatment of psychotic diseases or disorders, wherein the salt preferably is or comprises crystalline Asenapine malonate form I or crystalline Asenapine citrate form I.

(13) Pharmaceutical composition comprising one or more crystalline polymorphically stable salts, in particular in anhydrous form, of Asenapine with an organic di-acid or tri-acid according to any of items 1-5 or obtainable or obtained according to the process of any of items 6-11.

(14) Pharmaceutical dosage form comprising one or more crystalline polymorphically stable salts, in particular in anhydrous form, of Asenapine with an organic di-acid or tri-acid according to any of items 1-5 or obtainable or obtained according to the process of any of items 6-11.

(15) Pharmaceutical composition or dosage form of items 13 or 14, wherein at least 90 wt. %, further preferred at least 95 wt. %, even further preferred at least 98 wt. %, of Asenapine being present in said composition or dosage form is a crystalline polymorphically stable salt of Asenapine with an organic di-acid or tri-acid as described herein, preferably crystalline Asenapine malonate form I, and/or crystalline Asenapine citrate form I.

LIST OF FIGURES

FIG. 1: X-ray powder diffraction pattern of crystalline Asenapine malonate form I.

Figure 2:
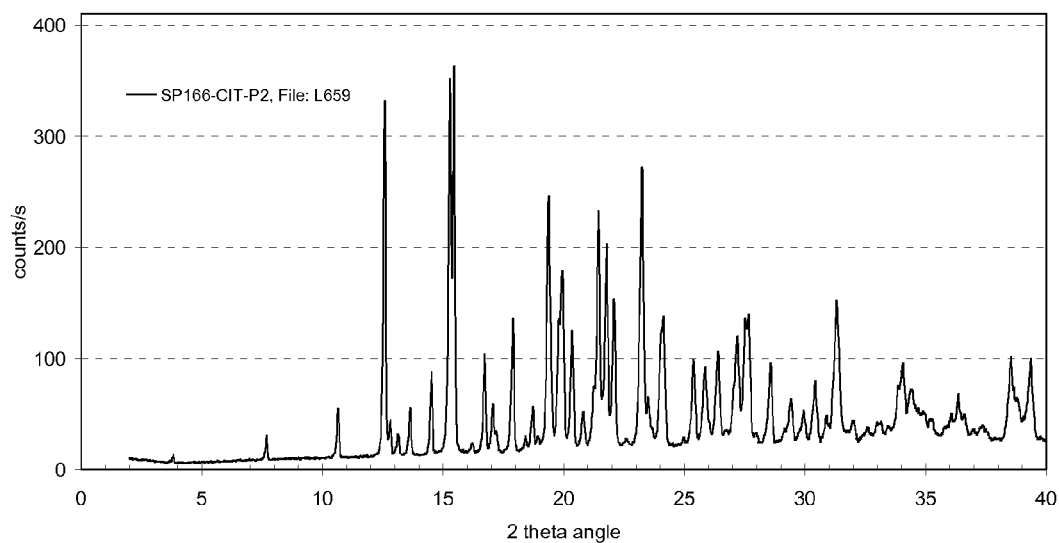

FIG. 2: X-ray powder diffraction pattern of crystalline Asenapine citrate form I.

DETAILED DESCRIPTION

The polymorphic form of Asenapine maleate as presently used in medicaments has the above described drawbacks. Although Asenapine maleate represents a salt of Asenapine with a di-acid, it has unexpectedly been found in the context of the invention that particularly di-acids and tri-acids can be used for providing Asenapine salts having desirable properties. Preferably, the Asenapine salt according to the invention does not represent Asenapine.

Trans-5-chloro-2-methyl-2,3,3a,12b-tetrahydro-1H-dibenz[2,3:6,7]oxepino[4,5-c]pyrrole (Asenapine/Asenapine free base) has a structure according to Formula I:

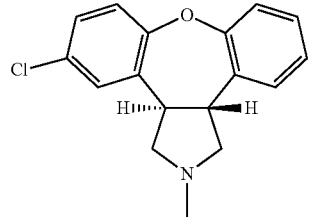

formula I

The invention refers to crystalline salts of Asenapine. In one aspect, the invention refers to a crystalline polymorphically stable salt, preferably in anhydrous form, of trans-5-chloro-2-methyl-2,3,3a,12b-tetrahydro-1H-dibenz[2,3:6,7] oxepino[4,5-c]pyrrole (Asenapine) with an organic di-acid or tri-acid, wherein said salt has a solubility in water at 25° C. of more than 2.4 mg/ml, calculated as free base and wherein the polymorphic stability is such that at least 90 wt. % of said salt does not change its crystal structure or maintains its crystal structure upon stirring in acetonitrile for 96 hours at a temperature of 20° C.

Also preferred, at least 91 wt. %, further preferred at least 92 wt. %, further preferred at least 93 wt. %, further preferred at least 94 wt. %, further preferred at least 95 wt. %, further preferred at least 96 wt. %, further preferred at least 97 wt. %, further preferred at least 98 wt. %, further preferred at least 99 wt. % or substantially/essentially all of the salt does not change its crystal structure or maintains its crystal structure upon stirring in acetonitrile for 96 hours at a temperature of 20° C. Particularly preferred, the X-ray powder diffraction reflection pattern does not change during the testing, i.e. no additional peaks (of a new polymorphic crystal form of said salt) can be identified, when comparing a sample of the salt prior to the polymorphic stability testing with a sample that has been subjected to stability testing as described in detail below. In one embodiment, the polymorphic stability test as described above is carried out by using acetonitrile in admixture with water (90:10 by volume) The polymorphic stability testing method as described herein allows for efficient testing and identifying polymorphic salts according to the invention.

The polymorphic stability of the salt according to the invention is preferably measured according to the method described below.

The Asenapine salts according to the invention have a solubility in water of at least 2.4 mg/ml, but may also have a solubility of at least 3.9 mg/ml. A typical maximum solubility of the salts according to the invention can e.g. be 30 mg/ml, 20 mg/ml or 15 mg/ml. The solubility of the salts is determined as described below.

Organic di-acid and tri-acid according to the invention can be any organic acids having two or three acid functions, wherein the acid functions preferably are carboxylic acid functions. The organic di-acids or tri-acids may have 3 to 20, further preferred 3 to 14, preferably 3 to 6 carbon atoms in total. They may represent saturated or unsaturated, preferably saturated, carboxylic di-acids or tri-acids. The organic acids according to the invention can optionally be substituted, e.g. with heteroatoms, however, the may only comprise the acid functions and optionally additional hydroxy or carboxy Preferably, the organic di-acid according to the invention is malonic acid ($C_3H_4O_4$) or citric acid ($C_6H_8O_7$). Preferably said salt is an anhydrous salt of Asenapine with malonic acid or citric acid.

The term "anhydrous form" as used in the context of the invention means that the salt contains less than a stoichiometric amount of water preferably less 1 wt. % of water.

Preferably, the molar ratio of Asenapine to the organic di-acid or tri-acid in said salt is between 1:1.3 to 1.3:1, preferably about 1:1. The ratio of Asenapine to the organic di-acid or tri-acid can be determined by H-NMR spectroscopy and/or elementary analysis.

In one aspect there are provided crystal structures of novel 1:1 salts of Asenapine with an organic di-acid or tri-acid of Formula II ($H_2O$ molecules optionally being present in the salt are not shown):

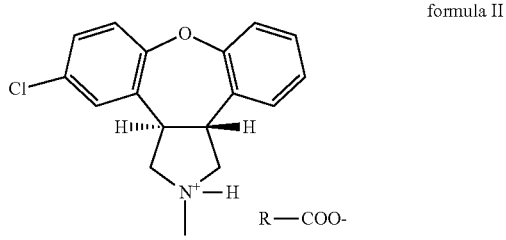

formula II wherein R is chosen so that R—COO$^-$ represents an organic di-acid or tri-acid, preferably malonate or citrate, wherein one acid function is deprotonated. Water can be present in the salts according to the invention in an amount of 0 to 4 molecules per Asenapine molecule, or 0 to 2 molecules per Asenapine molecule, preferably the amount of water is less than 1 molecule per Asenapine molecule (i.e. less than a stoichiometric amount of water). In one embodiment, the water uptake of the salt according to the invention is less than 3 wt. %, preferably less than 2 wt. %, preferably less than 1 wt. %, preferably less than 0.5 wt. %. The water uptake can be determined as described below.

In a one embodiment provided is a crystalline salt of Asenapine in form of a malonate. Crystalline Asenapine malonate form I of the invention is characterized by X-ray powder diffraction reflections comprising peaks at two theta angles of about 8.5°±0.2°, 19.5°±0.2°, 23.1°±0.2°, 23.7°±0.2° and 24.2°±0.2°. Crystalline Asenapine malonate form I is preferably characterized by a PXRD pattern substantially in accordance with FIG. 1, in particular the PXRD pattern comprises the peaks as given in Table 3.

The Asenapine malonate may contain small amounts of water. Dynamic vapor experiments showed that the water uptake even up to 95% rel. humidity is preferably very small, e.g. less than about 0.2%, thus the crystalline Asenapine malonate may be completely non-hygroscopic.

The aqueous solubility of the malonate of the invention was determined to be 3.9 mg/ml at 25° C. calculated as free base. The aqueous solubility was determined after 40 hours of suspension equilibration at 25° C. Thereafter, the suspensions were filtered and the concentration in the liquid phase was determined by HPLC.

In another embodiment provided is a crystalline salt of Asenapine in form of a citrate.

Crystalline Asenapine citrate form I of the invention is characterized by X-ray powder diffraction reflections comprising peaks at two theta angles of about 12.6°±0.2°, 15.3°±0.2°, 15.5°±0.2°, 19.4°±0.2° and 23.2°±0.2°. The crystalline citrate of the invention can be further characterized by a PXRD pattern substantially in accordance with FIG. 2, in particular the PXRD pattern comprises the peaks as given in Table 1.

In general, the Asenapine salts described herein are preferably characterized by their PXRD pattern, i.e. the peaks as given in the respective peak tables. Particularly suitable for characterizing the salts are the peaks having an intensity of vs (very strong), s (strong) and m (medium).

The hygroscopic nature of the citrate salt was investigated by dynamic vapor sorption. The citrate may absorb about 1.5% of water and most of the water uptake occurs above 80% relative humidity. Therefore the Asenapine citrate of the invention is not or only very slightly hygroscopic.

The aqueous solubility of the citrate of the invention was determined to be 2.4 mg/ml at 25° C. calculated as free base. The aqueous solubility was determined after 40 hours of suspension equilibration at 25° C. Thereafter, the suspensions were filtered and the concentration in the liquid phase was determined by HPLC.

In one embodiment, the crystalline salt comprises or consists of (i) crystalline Asenapine malonate form I or (ii) crystalline Asenapine citrate form I, wherein (i) crystalline Asenapine malonate form I is characterized by X-ray powder diffraction reflections comprising peaks at two theta angles of about 19.5°±0.2°, 23.7°±0.2°, 8.5°±0.2°, 23.1°±0.2°, and 24.2°±0.2°, and (ii) crystalline Asenapine citrate form I is characterized by X-ray powder diffraction reflections comprising peaks at two theta angles of about 15.5°±0.2°, 15.3°±0.2°, 12.6°±0.2°, 23.2°±0.2°, and 19.4°±0.2°.

Crystalline Asenapine malonate form I and crystalline Asenapine citrate form I have a solubility in water at 25° C. of more than 2.0 mg/ml, calculated as free base, and a polymorphic stability of such that more than 90 wt. % of said salt does not change its crystal structure upon stirring in acetonitrile or a mixture of acetonitrile and water for 96 hours at a temperature of 20° C. Thus, in one aspect, the invention refers to crystalline Asenapine malonate form I and crystalline Asenapine citrate form I.

Preferably, the crystalline salt comprises at least 80 wt. %, further preferred at least 90 wt. %, even further preferred at least 95 wt. %, and most preferably at least 98 wt. % of one polymorphic form of Asenapine with an organic di-acid or tri-acid, preferably, the polymorph is crystalline Asenapine malonate form I or crystalline Asenapine citrate form I.

The invention also refers to a process for preparing a crystalline polymorphically stable salt, preferably in anhydrous form, of trans-5-chloro-2-methyl-2,3,3a,12b-tetrahydro-1H-dibenz[2,3:6,7]oxepino[4,5-c]pyrrole (Asenapine) with an organic di-acid or tri-acid comprising the steps of:
  a) combining Asenapine free base with an organic di-acid or tri-acid in an organic solvent or organic solvent mixture, optionally comprising water; optionally under stirring, and
  b) obtaining said crystalline polymorphically stable Asenapine salt.

Preferably, the organic di-acid or tri-acid is a carboxylic di-acid or carboxylic tri-acid, preferably an unsaturated $C_3$-$C_{14}$ carboxylic di-acid or tri-acid, further preferred malonic acid or citric acid. Preferred di-acids and tri-acids are also described above.

The amount of organic di-acid or tri-acid is not critical and may e.g. be 0.8 to 2 moles of organic di-acid or tri-acid per mole of Asenapine. However, a molar excess of organic di-acid or tri-acid to Asenapine base is preferred for maximizing the yield. For example an amount of at least 2 or of at least 5 moles, also of at least 10 moles %, to about 50 moles %, of the organic di-acid or tri-acid can be used.

The temperature in the crystallization step is not critical, e.g. temperatures of about ambient temperature (e.g. 15° C. or 20° C.) up to the boiling point of the solvent may be used. Conveniently, the crystallization is performed at ambient temperature and the suspension may then be cooled or solvent is partly evaporated to complete the crystallization.

In one embodiment, step (a) is carried out at a temperature of between 15° C. and the boiling temperature of the organic solvent or organic solvent mixture optionally containing water, preferably under stirring (e.g. 600 rpm), for a period of time sufficient to induce crystallization, preferably of between 1 hour and two weeks, preferably between one day and one week.

Additionally preferred, step (a) is carried out in the presence of seed crystals.

Within the meaning of the invention, the term "seed crystals" refers to that type of crystals that help produce the desired crystal form of Asenapine salt. For example, if it is desired to produce crystalline Asenapine malonate form I or crystalline Asenapine citrate form I, the seed crystals to be used to enhance the crystallization process can e.g. be crystals of crystalline Asenapine malonate form I or crystalline Asenapine citrate form I.

When preparing Asenapine salts in anhydrous form, it is preferred that water—if present in the reaction mixture—is removed e.g. by distillation.

Combining Asenapine free base with an organic di-acid or tri-acid in an organic solvent or organic solvent mixture and obtaining said crystalline polymorphically stable Asenapine salt can be carried out by methods known in the art. For example, the organic di-acid or tri-acid can be added to the Asenapine free base in the organic solvent or solvent mixture in pure form or can be dissolved in an organic solvent or water as defined herein. According to one option, in step (a), Asenapine free base is dissolved in the organic solvent or organic solvent mixture and then the organic di-acid or tri-acid is added, preferably under stirring. According to another option, a solution of Asenapine free base is added to a solution of organic di-acid or tri-acid. Preferably, the solvent system used for dissolving Asenapine free base is the same as used for dissolving the organic di-acid or tri-acid. In one embodiment, the organic di-acid or tri-acid is dissolved in water.

Crystallization may be completed by addition of an anti-solvent. In another embodiment, crystallization may be enhanced by cooling the reaction mixture obtained in step (a) or by partly removing organic solvent from the reaction mixture either during or after step (a).

Additionally preferred, obtaining said crystalline Asenapine salt in step (b) comprises isolation of said salt by filtration, washing the obtained salt and drying said salt.

In a preferred embodiment of the process, the crystalline polymorphically stable Asenapine salt obtained in step (b) is crystalline Asenapine malonate form I or crystalline Asenapine citrate form I.

The solvent or solvent mixture that is used in the process in step (a) preferably comprises or consists of one or more organic solvents from the group consisting of esters, preferably acetic acid $C_1$-$C_6$ alkylesters, most preferably ethylacetate; alcohols, preferable $C_1$-$C_5$ alcohols, e.g. methanol, ethanol or propanol or mixtures thereof; mixtures of acetic acid $C_1$-$C_6$ alkylesters and $C_1$-$C_6$ alcohols, preferable ethyl acetate and a $C_1$-$C_5$ alcohol, preferably ethanol; ketones, preferably acetone; combinations of acetic acid $C_1$-$C_6$ alkylesters; optionally in the presence of water A suitable amount of solvent or solvent mixture can easily be chosen by a person skilled in the art. The amount of solvent or solvent mixture is chosen in order to at least dissolve Asenapine free base In one embodiment, the crystalline Asenapine malonate form I of the invention may be prepared by
  a) combining Asenapine free base with malonic acid in a suitable solvent, and
  b) crystallizing Asenapine malonate optionally in the presence of seeds.

Preferred solvents include but are not limited to esters, preferably acetic acid $C_1$-$C_4$ alkylesters, most preferably ethylacetate, or mixtures thereof; alcohols, preferable $C_1$-$C_4$ alcohols, e.g. methanol, ethanol or propanol or mixtures thereof; or mixtures of acetic acid $C_1$-$C_4$ alkylesters and $C_1$-$C_4$ alcohols.

The malonic acid may be used as such or as solution in above mentioned solvents or solvent mixtures. The amount of malonic acid is not critical, e.g. 0.8 to 2 moles of malonic acid per mole of Asenapine may be used.

The crystalline malonate of the invention is polymorphically stable, e.g. by stirring a suspension of the malonate in water at 25° C. no polymorph conversion was observed. No polymorph conversion was also observed stirring a suspension of the crystalline Asenapine malonate of the invention for 4 days at ambient temperature.

In one embodiment, the crystalline citrate of the invention may be prepared by
  a) combining Asenapine free base with citric acid in a suitable solvent, and
  b) crystallizing Asenapine citrate optionally in the presence of seeds.

Preferred solvents include but are not limited to ketones, more preferably acetone; acetic acid $C_1$-$C_6$ alkylesters, preferably ethyl acetate; combinations of acetic acid $C_1$-$C_6$ alkylesters or combinations of acetic acid $C_1$-$C_6$ alkylesters with alcohols and/or ketones, preferable ethyl acetate and a $C_1$-$C_5$ alcohol, preferably ethanol; optionally in the presence of water.

The amount of citric acid is not critical and may e.g. be 0.8 to 2 moles per mole of Asenapine. However, a molar excess of citric acid to Asenapine base is preferred for maximizing the yield e.g. an excess of about 10 molar % to about 50 molar %. The temperature in the crystallization step is not critical, e.g. temperatures of about ambient temperature up to the boiling point of the solvent may be used. Conveniently, the crystallization is performed at ambient temperature and the suspension may then be cooled to complete the crystallization.

Citric acid anhydrous citric acid or the monohydrate are suitable sources for the preparation of the crystalline Asenapine citrate salt. The citric acid may be used as such or as a solution, preferably as solution in water, e.g. at about 20% to about 60% (w/w) solution in water. The ratio of organic solvent to water in the crystallization step is not critical, however to maximize yield a ratio of water to organic solvent(s), preferably acetone, in the crystallization step is from about 7:3 to 9:1 (v/v).

The Asenapine citrate of the invention is polymorphically stable, e.g. it does not change its polymorphic form in a suspension in water at 25° C. respectively equilibration in acetonitrile for 5 days, thus eliminating the problem formulating the known maleate according to WO 95/23600 and WO 2006/16135.

Additionally preferred, step (a) is carried out at a temperature of between 15° C. and the boiling temperature of the solvent or solvent mixture preferably under stirring (e.g. 600 rpm), for a period of time sufficient to induce crystallization, preferably of between 1 hour and two weeks, preferably between one day and one week.

The invention also refers to crystalline salts of Asenapine obtainable or obtained according to the process as described above.

The invention also refers to a crystalline polymorphically stable salt, in particular in anhydrous form, of Asenapine with an organic di-acid or tri-acid according to the invention as medicament, preferably for the treatment of psychotic diseases or disorders, wherein the salt preferably is or comprises crystalline Asenapine malonate form I or crystalline Asenapine citrate form I. Other preferred salts are described above.

The invention also refers to a pharmaceutical composition comprising one or more crystalline polymorphically stable salts, in particular in anhydrous form, of Asenapine with an organic di-acid or tri-acid according to the invention. Preferred salts are described above.

The invention also refers to a pharmaceutical dosage form comprising one or more crystalline polymorphically stable salts, in particular in anhydrous form, of Asenapine with an organic di-acid or tri-acid according to the invention. Preferably said pharmaceutical formulation or dosage form comprises one or more salts of the invention and at least one pharmaceutically acceptable carrier or diluent. Preferred salts are described above.

In one embodiment of the pharmaceutical composition or dosage form, at least 80 wt. %, further preferred at least 90 wt. %, also preferred at least 95 wt. %, and also preferred at least 98 wt. %, of Asenapine being present in said composition or dosage form is a crystalline polymorphically stable salt of Asenapine with an organic di-acid or tri-acid, preferably crystalline Asenapine malonate form I, and/or crystalline Asenapine citrate form I.

The crystalline malonate of the invention and the crystalline citrate of the invention may be formulated as disclosed for example in Example 16 of WO 2006/106135 by mixing the novel crystalline salt into a gelatin/mannitol/water mixture and freeze drying, preferably after dosing into preformed pockets. Other ways of formulating Asenapine salts into pharmaceutical compositions or dosage forms are known in the art.

Powder X-ray diffraction: PXRD was carried out with a Bruker D8 Advance powder X-ray diffractometer using $Cu_{K\alpha}$ radiation in reflection (Bragg-Brenatno) geometry. $2\theta$ values usually are accurate within an error of ±0.1-0.2°. The samples were generally prepared without any special treatment other than the application of slight pressure to get a flat surface. Two different Silicon single crystal sample holder types were used:

a) a standard holder with 0.1 mm in depth, and b) a 0.5 mm depth sample holder with 12 mm cavity diameter. Normally samples were measured uncovered. The tube voltage was 40 kV and current was 40 mA. The PXRD diffractometer is equipped with a LynxEye detector. A variable divergence slight was used with a 3° window. The step size was 0.02° $2\theta$ with a step time of 37 seconds. The samples were rotated at 0.5 rps during the measurement.

Raman spectroscopy and Raman microscopy: FT-Raman spectra were recorded on a Bruker RFS 100 FT-Raman system with a near infrared Nd:YAG laser operating at 1064 nm and a liquid nitrogen-cooled germanium detector. 64 scans with a resolution of 2 $cm^{-1}$ were accumulated in the range from 3500 to 50 $cm^{-1}$. In general, 100 mW laser power was used.

DSC:

Differential scanning calorimetry was carried out with a Perkin Elmer DSC-7 instrument (closed gold sample pan or gold-plated steel sample pan, heating rates 10 and 20 K/min).

TG-FTIR:

Thermogravimetric measurements were carried out with a Netzsch Thermo-Microbalance TG 209 coupled to a Bruker FTIR Spectrometer Vector 22 (sample pans with a pinhole, $N_2$ atmosphere, heating rate 10 K/min).

Solvents:

For all experiments, Fluka or Merck analytical grade solvents were used.

Approximate Solubility:

Approximate solubilities were determined by a stepwise dilution of a suspension of about 10 mg SP166-FB-P1 in 0.1 ml of solvent. If the substance was not dissolved by addition of a total of 10 ml solvent, the solubility is indicated as less than 1 mg/ml.

Water Uptake of the Salt:

The water uptake of the salts according to the invention is determined by dynamic vapor sorption by exposing the salt to an atmosphere of 95% humidity.

Determining Solubility of Asenapine Salts:

The aqueous solubility of Asenapine salts is determined in water after 48 hours of suspension equilibration at 25° C. Thereafter, the suspension is filtered and the concentration in the liquid phase was determined by HPLC as described above.

HPLC method:

An HPLC instrument from TSP (UV3000, AS3000, P4000, SCM1000 using software version 4.1) was used in combination with a column from Waters (XTerra MS 018, 4.6×100 mm, 5 μm (CC01A)). The mobile phase A was $H_2O$/ACN 95:5 with 0.1% TFA, and mobile phase B was $H_2O$/ACN 5:95 with 0.1% TFA. The reference concentration was 0.09 mg/mL. The Asenapine peak appeared at a retention time 4.0-4.1 min. The method was isocratic with 70% mobile phase A and 30% mobile phase B at 0 min and after 10 min at a flow of 1.0 mL/min. The injection volume was 10 μL and the detection wavelength 202 nm.

Determining Polymorphic Stability:

According to the invention, polymorphic stability is such that said the salts according to the invention do not change their crystal structure, i.e. maintain their crystal structure upon stirring in acetonitrile (or a mixture of acetonitrile and water as defined above) for 96 hours at a temperature of 20° C. The stability test is carried out by stirring the sample salt at 600 rpm in an amount of approximately 0.1 g/ml acetonitrile and optionally water as defined above. After 96 hours of stirring, the salt is removed by filtration and is dried and then subjected to X-ray powder diffraction analysis.

REFERENCE EXAMPLE 6.43 g of Asenapine maleate were added with stirring to a mixture of 40 ml of 1 M (molar) NaOH and 320 ml of methyl tert. butylether. The mixture was stirred for 10 min and the layers were separated. The aqueous layer was extracted with 320 ml of methyl-tert. butylether. The combined organic layers were extracted with 150 ml of water.

The organic layer was dried with 13.6 g of sodium sulfate. The suspension was filtered and the solution was concentrated in vacuo at about 40° C. and 20 ml.

Yield:
3.77 g of Asenapine free base as an oil.

Example 1

Preparation of Crystalline Asenapine Citrate Form I Seed Crystals 140 mg Asenapine free base (~0.5 mmol) was dissolved in a mixture 8.0 ml of a 0.05 M stock solution of citric acid (Fluka #24788) in ethanol and 2.0 ml 0.05 M stock solution of citric acid in ethyl acetate (~0.5 mmol citric acid). A part of the solvent mixture was evaporated under a weak flow of nitrogen about 20 ml/min and after evaporation of about 8 ml of the solvent mixture 2.0 ml ethyl acetate was added and a suspension was obtained within a few hours. More solvent was evaporated by stirring the vial with the cap open and after four days the resulting concentrated suspension was diluted with 1.0 ml ethyl acetate and the obtained product was separated by filtration. The solid product was dried under vacuum at r.t. for about 16 hours, then investigated by H-NMR, powder X-ray diffraction, TG-FTIR, and light microscopy. H-NMR spectroscopy showed an Asenapine citrate salt with an approximate 1:1 ratio of Asenapine to citric acid. Light microscopy revealed that the salt was crystalline and it showed a PXRD pattern as depicted in FIG. 2 with the most important peaks as provided in Table 1. TG-FTIR did not reveal any significant mass loss upon heating to 180° C. at a rate of 10 K/min.

The Raman spectrum of the crystalline citrate comprises peaks at wavenumbers of about 1602 cm$^{-1}$, 1581 cm$^{-1}$, 1048 cm$^{-1}$, 711 cm$^{-1}$ and 346 cm$^{-1}$.

TABLE 1

PXRD peak table for crystalline Asenapine citrate form I

| Angle 2θ | d-spacings [Å] | qualitative relative intensity |
|---|---|---|
| 12.6 | 7.03 | vs |
| 14.5 | 6.09 | m |
| 15.3 | 5.80 | vs |
| 15.5 | 5.73 | vs |
| 16.7 | 5.30 | m |
| 17.9 | 4.95 | s |
| 18.7 | 4.74 | m |
| 19.4 | 4.58 | vs |
| 19.8 | 4.48 | s |
| 19.9 | 4.45 | s |

TABLE 1-continued

PXRD peak table for crystalline Asenapine citrate form I

| Angle 2θ | d-spacings [Å] | qualitative relative intensity |
|---|---|---|
| 20.4 | 4.36 | s |
| 21.3 | 4.18 | m |
| 21.4 | 4.14 | s |
| 21.8 | 4.08 | s |
| 22.1 | 4.02 | s |
| 23.2 | 3.82 | vs |
| 24.1 | 3.69 | s |
| 25.4 | 3.51 | m |
| 25.9 | 3.44 | m |
| 26.4 | 3.38 | m |
| 27.2 | 3.28 | s |
| 27.5 | 3.24 | s |
| 27.7 | 3.22 | s |
| 28.6 | 3.12 | m |
| 30.4 | 2.94 | m |
| 31.2 | 2.87 | m |
| 31.3 | 2.85 | s |
| 33.9 | 2.65 | m |
| 34.0 | 2.63 | m |

Example 2

Preparation of the Crystalline Asenapine Citrate Form I 150 mg Asenapine free base was dissolved in 3.0 ml acetone and to this solution was added 0.25 ml of a 2M stock solution of citric acid (Fluka #24788) in water. After seeding with a few of crystalline citrate salt according to example 1 a white suspension begins to form after 5 minutes. Stirring was continued at room temperature, and on the next day the suspension was filtered and the product dried under vacuum at room temperature for about 18 hours. The obtained sample was characterized by powder X-ray diffraction, which confirmed that the same crystalline form as in example 1 was obtained. Further investigation by elemental composition analysis showed a composition that is consistent with a 1:1 salt of Asenapine and citric acid as provided in Table 2. Differential scanning calorimetry shows a single melting peak at 174° C. with an enthalpy of fusion of about 116 J/g.

TABLE 2

Result of the elemental composition analysis for crystalline Asenapine citrate form I

| Element | % Found | % Expected |
|---|---|---|
| C | 57.7 | 57.8 |
| H | 5.1 | 5.1 |
| N | 3.1 | 2.9 |
| O | 27.3 | 26.8 |
| Cl | 7.4 | 7.4 |

Example 3

Preparation of Crystalline Asenapine Citrate Form I 500 mg Asenapine free base (~1.7 mmol) were dissolved in 1.0 ml acetone and 320 mg of citric acid (Fluka #24788) which was dissolved in 1.0 ml water was added to the solution containing the free base. This solution was then seeded with a few mg of crystalline citrate salt according to example 1 and to the very thin suspension 2.0 ml water was added and stirred was performed while keeping the vial open letting some acetone evaporate. On the next day the obtained suspension was filtered and about 633 mg of solid product was obtained after drying under vacuum at r.t. for about 18 hours. Powder X-ray diffraction of the obtained solid product showed that the same crystalline form as in example 1 was obtained.

Example 4

Stability of the Crystalline Form of Crystalline Asenapine Citrate Form I with Respect to Polymorph Conversion 77 mg crystalline Asenapine citrate form I according to Example 2 was suspended in 2.0 ml water and the glass vial was placed on a standard laboratory shaker (Eppendorf) at 25° C. and 600 rpm for two days. After two days of equilibration the suspension was filtered and the recovered solid investigated by PXRD which confirmed the presence of the same crystalline form as in example 2; i.e., no phase transformation was observed. The aqueous solubility was determined by measuring the concentration of asp in the filtered solution by HPLC.

Example 5

Stability of Crystalline Asenapine Citrate Form I with Respect to Polymorph Conversion To 192 mg of Asenapine citrate according to example 2 was added 2.0 ml acetonitrile and the obtained suspension was stirred at room temperature for five days. After five days of equilibration the suspension was filtered and the recovered solid investigated by PXRD which confirmed the presence of the same crystalline form as in example 2; i.e., no phase transformation was observed.

Example 6

Preparation of Crystalline Asenapine Malonate Form I Seed Crystals 100 mg asp free base was dissolved in 3.0 ml ethyl acetate and to this solution 165 μl of a 2.0 M stock solution of malonic acid (Fluka #63290) in methanol was added. The solvents from the clear solution were evaporated under nitrogen and to the oily residue 1.0 ml ethyl acetate was added. After a few hours stirring at room temperature a suspension was obtained which was filtered. About 104 mg of solid product was obtained after short drying in air at room temperature. Investigation of the obtained sample by powder X-ray diffraction revealed a crystalline material with a PXRD pattern as shown in FIG. 1 and peaks as indicated in Table 3. Furthermore, the crystalline product was characterized by DSC which showed a single melting peak at 164° C. with an enthalpy of fusion of about 163 J/g. The elemental composition analysis confirmed a malonate salt with a 1:1 stoichiometry of Asenapine to malonic acid as provided in Table 4.

TABLE 3

PXRD peak table for crystalline Asenapine malonate form I

| Angle 2θ | d-spacings [Å] | qualitative relative intensity |
|---|---|---|
| 8.5 | 10.40 | vs |
| 16.4 | 5.38 | m |
| 17.0 | 5.21 | s |
| 18.6 | 4.78 | s |
| 19.5 | 4.54 | vs |
| 19.7 | 4.49 | w |
| 20.7 | 4.28 | w |
| 23.1 | 3.84 | s |
| 23.7 | 3.76 | s |
| 24.2 | 3.68 | m |
| 24.7 | 3.61 | s |
| 25.5 | 3.49 | m |
| 25.8 | 3.46 | m |
| 26.6 | 3.35 | m |
| 27.0 | 3.30 | m |
| 27.9 | 3.19 | m |
| 28.4 | 3.14 | m |
| 30.3 | 2.95 | w |
| 30.5 | 2.93 | m |
| 30.7 | 2.91 | w |
| 30.9 | 2.89 | w |
| 31.7 | 2.82 | w |
| 32.4 | 2.76 | m |
| 32.7 | 2.74 | w |
| 33.8 | 2.65 | w |
| 34.4 | 2.61 | w |
| 34.7 | 2.58 | w |
| 36.3 | 2.47 | w |
| 37.4 | 2.40 | w |

TABLE 4

Result of the elemental composition analysis of crystalline Asenapine malonate form I

| Element | % effectively found | % normalized* | % expected |
|---|---|---|---|
| C | 60.25 | 61.3 | 61.6 |
| H | 5.15 | 5.2 | 5.2 |
| N | 3.64 | 3.7 | 3.6 |
| O | 20.11 | 20.5 | 20.5 |
| Cl | 9.11 | 9.3 | 9.1 |

*Since the sum of all measured components in column 2 was only 98.25% these data was normalized to 100% and compared with the theoretically expected values in column 4.

Example 7

Preparation of Crystalline Asenapine Malonate Form I 300 mg asp free base was dissolved in 0.5 ml ethyl acetate and to this solution was added 109.4 mg of malonic acid (Fluka #63290) dissolved in 3 ml ethyl acetate. To the clear solution a few mg of asp malonate according to Example 6 was added as seed crystals. After about six hours of stirring at room temperature a suspension was obtained which was filtered. The solid product was dried under vacuum at room temperature for about 20 hours and an estimated yield of about 300 mg was obtained. H-NMR analysis confirmed a 1:1 salt of Asenapine with malonic acid. Furthermore, the produced salt was characterized and by FT-Raman spectroscopy and by powder X-ray diffraction which indicated that the same crystalline form as in example 6 was obtained. Light microscopy revealed very small crystalline particles and TG-FTIR showed only a small mass loss of about 1.8% upon heating to 150° C. at a rate of 10 K/min.

The Raman spectrum of the crystalline malonate comprises peaks at wavenumbers of about 1065 cm$^{-1}$, 1584 cm$^{-1}$, 1215 cm$^{-1}$, 843 cm$^{-1}$, 711 cm$^{-1}$ and 341 cm$^{-1}$.

Example 8

Preparation of Crystalline Asenapine Malonate Form I 511 mg Asenapine free base was dissolved in 1.0 ml 2-propanol and to this solution was added 186 mg of malonic acid (Fluka #63290) which was dissolved in 4 ml 2-propanol. The clear solution was seeded with 23 mg of crystalline malonate salt according to example 6 and stirring at r.t. was continued at room temperature until the next day (about 20 hours). The suspension was filtered, and after drying at room temperature for about 20 hours under vacuum about 640 mg of crystalline solid product was obtained. Investigation by powder X-ray diffraction showed that the same crystalline form as in example 6 was obtained.

Example 9

Stability of the Crystalline Form of Crystalline Asenapine Malonate Form I with Respect to Polymorph Conversion 97 mg crystalline Asenapine malonate form I according to example 7 was suspended in 2.0 ml water and the glass vial placed on a standard laboratory shaker (Eppendorf) at 25° C. and 600 rpm for two days. After two days of equilibration the suspension was filtered and the recovered solid investigated by PXRD which confirmed the presence of the same crystalline form as in example 7; i.e., no phase transformation was observed. The aqueous solubility was determined by measuring the concentration of asp in the filtered solution by HPLC.

Example 10

Stability of the Crystalline Form of Crystalline Asenapine Malonate Form I with Respect to Polymorph Conversion 108 mg of crystalline Asenapine malonate form I according to example 8 was suspended in 2.0 ml acetonitrile-acetone 1:1 and the resulting suspension was stirred at room temperature for four days. Then the suspension was filtered and the obtained solid investigated by powder X-ray diffraction which confirmed the presence of the same crystalline form as in example 8; i.e., no phase transformation was observed.

Cited Documents
WO 98/54186;
EP 0569096;
WO 2006/106135;
Funke et. al. (Arzneim.-Forsch./Drug Res. 40, 1999, 536-539);
WO 2009/135091,
Peter van Hoof et al. (Amorphous Pharmaceutical Materials, September 2009),
US2008/0306133 A1,
WO 95/023600.

The invention claimed is:

1. A crystalline polymorphically stable salt, in anhydrous form, of trans-5-chloro-2-methyl-2,3,3a,12b-tetrahydro-1H-dibenz[2,3:6,7]oxepino[4,5-c]pyrrole (Asenapine) with an organic di-acid or tri-acid, wherein the organic di-acid or tri-acid is malonic acid or citric acid, wherein said salt has a solubility in water at 25° C. of more than 2.0 mg/ml, calculated as free base and wherein the polymorphic stability is such that at least 90 wt. % of said salt maintains its crystal form upon stirring in acetonitrile for 96 hours at a temperature of 20° C.

2. The crystalline salt of claim 1, wherein the molar ratio of Asenapine to the organic di-acid or tri-acid in said salt is between 1:1.3 to 1.3:1.

3. The crystalline salt of claim 1, wherein the organic di-acid or tri-acid is a carboxylic di-acid or carboxylic tri-acid.

4. A crystalline salt of Asenapine according to claim 1, which comprises (i) crystalline Asenapine malonate form I and/or (ii) crystalline Asenapine citrate form I, wherein
 (i) crystalline Asenapine malonate form I is characterized by X-ray powder diffraction reflections (Cu Kα radiation) comprising peaks at two theta angles of about 19.5°±0.2°, 23.7°±0.2°, 8.5°±0.2°, 23.1°±0.2°, and 24.2°±0.2°, and
 (ii) crystalline Asenapine citrate form I is characterized by X-ray powder diffraction reflections (Cu Kα radiation) comprising peaks at two theta angles of about 15.5°±0.2°, 15.3°±0.2°, 12.6°±0.2°, 23.2°±0.2°, and 19.4°±0.2°.

5. A process for preparing a crystalline polymorphically stable salt according to claim 1 comprising the steps of:
 a) combining Asenapine free base with an organic di-acid or tri-acid in an organic solvent or organic solvent mixture, optionally comprising water, and
 b) obtaining said crystalline polymorphically stable Asenapine salt.

6. The process of claim 5, wherein the organic di-acid or tri-acid is a carboxylic di-acid or carboxylic tri-acid, which is a saturated $C_3$-$C_{14}$ carboxylic di-acid or tri-acid.

7. The process of claim 5, wherein step (a) is carried out in the presence of seed crystals.

8. The process of claim 5, wherein the crystalline polymorphically stable Asenapine salt obtained in step (b) is crystalline Asenapine malonate form I or crystalline Asenapine citrate form I.

9. The process of claim 5, wherein the solvent or solvent mixture comprises one or more organic solvents from the group consisting of esters, alcohols, and ketones.

10. The process of claim 5, wherein step (a) is carried out at a temperature of between 15° C. and the boiling temperature of the solvent or solvent mixture under stirring.

11. A pharmaceutical composition comprising one or more crystalline polymorphically stable salts according to claim 1 and pharmaceutically acceptable excipients.

12. A pharmaceutical composition of claim 11, wherein at least 80 wt. % of Asenapine present in said composition is a crystalline polymorphically stable salt of Asenapine with an organic di-acid or tri-acid, which is crystalline Asenapine malonate form I, and/or crystalline Asenapine citrate form I.

* * * * *